United States Patent [19]

Tzodikov

[11] 4,411,881
[45] Oct. 25, 1983

[54] COMPOSITION AND METHOD FOR STABILIZING RADIOLABELED COMPOUNDS USING THIOCARBONYLATED DIETHYLENETRIAMINES

[75] Inventor: Nathan R. Tzodikov, Marshfield, Mass.

[73] Assignee: New England Nuclear Corporation, Boston, Mass.

[21] Appl. No.: 397,501

[22] Filed: Jul. 12, 1982

[51] Int. Cl.$^3$ .................. A61K 43/00; A61K 49/00
[52] U.S. Cl. ................................ 424/1.1; 436/8; 436/18; 252/644
[58] Field of Search ............... 424/1; 252/301.1, 478, 252/517; 436/8, 18

[56] References Cited

U.S. PATENT DOCUMENTS 3,876,550  4/1975  Holubee ........................ 252/47.5
3,919,095  11/1975  Okorodudu .................... 252/46.6
4,358,434  11/1982  Tzodikov et al. .................. 424/1

OTHER PUBLICATIONS

"Synthesis and Antiradiation Properties of Polymeric Dithiocarbamates", V. S. Etlis et al., UDC 615.849.1.015.25:547.496.2, translated from Khimiko-Farmatsevticheskii Zhurnal, vol. 10, No. 4, pp. 33–35, Apr. 1976.

"Synthése et Effets Radioprotecteurs d'Alkanebisdithiocarbamates disodiques, d'Acides ω-Aminoalkyldithiocarbamiques et de leurs dérives N,N'-Dimethylés," J. H. Barnes et al., Eur. J. Med. Chem. Chimca Therapeutica, Nov.-Dec. 1975, 10 N° 6, pp. 619–622.

Primary Examiner—Christine M. Nucker
Assistant Examiner—M. Moskowitz
Attorney, Agent, or Firm—Sewall P. Bronstein; George W. Neuner

[57] ABSTRACT

A stabilized composition comprising a solution of a radiolabeled compound and a diethylenetriamine is described. Preferred diethylenetriamines include, N,N-bis(2-aminoethyl) dithiocarbamic acid, di(2-dithiocarbamyl-ethyl) amine, and salts thereof.

23 Claims, No Drawings

COMPOSITION AND METHOD FOR STABILIZING RADIOLABELED COMPOUNDS USING THIOCARBONYLATED DIETHYLENETRIAMINES

BACKGROUND OF THE INVENTION

1. Field of the Invention

This invention relates to the stabilization of radiolabeled compounds, such as amino acids and nucleosides and particularly to certain thiocarbonylated amines useful for stabilizing such radiolabelled compounds.

2. Description of the Prior Art

An increasing number of radiolabeled compounds are being used in research for medical diagnosis and various other areas. However, the radiolytic decomposition of such compounds has been a constant problem. Without the addition of some type of stabilizer, a solution of such a compound may become unusable due to decomposition within a matter of weeks or less. This radiolytic decomposition of such compounds has been studied extensively. For example, the radiation chemistry of amino acids is reviewed in an article by J. Liebster and J. Kopeldova, *Radiation Biol.*, 1, 157 (1964) and the self-decomposition of radioactively labeled compounds is discussed in *Atomic Energy Review*, 10, 3–66 (1972), both of which are hereby incorporated herein by reference.

Although certain specific compounds have been suggested for stabilization, problems still exist. The latter article reviews the underlying causes and mechanisms of self-decomposition, "which are very complex and in some cases not well understood." (At pg. 3). After discussing the principal mechanisms by which decomposition occurs, the article notes generally at page 36 that buffers such as ammonium bicarbonate help to stabilize radiolabeled compounds, but care must be taken to insure that the buffer chosen does not interfere with the later use of the labeled compound. For example, phosphate buffers would interfere with phosphorylation reactions. Other compounds which have been suggested at various times are listed at page 35 and include benzyl alcohol, glycerol, cysteamine, and sodium formate. However, each of these are said to suffer due to their difficulty of removal. Another compound mentioned is ethanol which is said to work with many compounds. However, ethanol sometimes actually sensitizes certain nucleosides to radiation decomposition and thus it has been found not to be a universal panacea. Furthermore, if it will interfere with the reaction in which the radiolabeled compound is to be used, the ethanol must be removed by evaporation which may also contribute to decomposition.

Various compounds are suggested in *Atomic Energy Review*, above, for stabilization of radiolabeled compounds prone to oxidation including antioxidants such as butylated-hydroxytoluene, butylated-hydroxyanisole and mercaptoethanol. While not mentioned for use with radiolabeled compounds, the inhibition of autoxidation generally by certain amines has also been described in the prior art. Recent reviews on the inhibition of autoxidation are "Autoxidation" by R. Stroh, pg, 1049 in, *Methoden der Organischen Chemie* (Houben-Weyl), ed. E. Muller and O. Bayer, Vol. IV/Ib Oxidation II., Georgthieme Verlag, 1975, and *Encyclopedia of Chemical Technology*, Kirk Othmer, Interscience Publishers, New York. The utility of secondary dialkyl amines bearing full alpha-substitution (i.e., containing no hydrogens on the carbon atoms adjacent to the nitrogen) and secondary diarylamines (also without alpha-hydrogens) as antioxidants is known. However, the use of primary, secondary and tertiary amines, those containing alpha-hydrogens, in this regard is not known and, in fact, it has been suggested that such amines are not effective for this purpose. Such antioxidants have many of the same problems as other of the compounds discussed above, including, in addition, generally being insoluble in the solvents used to dissolve and store radiolabeled compounds for use in biological studies.

U.S. Pat. No. 3,876,550 describes lubricant compositions to improve the anti-oxidant and rust inhibiting properties of such lubricant compositions. The additive combination includes alkylene dithiocarbamate, but does not contain any suggestion for the use of such compounds as stabilizers for radiolabeled compounds.

V. S. Etlis et al., "Synthesis and Anti-Radiation Properties of Polymeric Dithiocarbamates", *Khimiko-Farmatsevticheskii Zhurnal*, Vol. 10, no. 4 pp. 33–35, April (1976) describes the synthesis and preparation of water soluble polymeric sodium and ammonium dithiocarbamates, indicates that they are useful as radiation protectors, and reports testing of such compounds in mice for protection against irradiation with $Co^{60}$ (1000 R, intensity 26–30 R/sec.) However, these compounds are not indicated as having any activity as stabilizers of radiolabeled compounds.

J. Barnes et al., *Eur. J. Med. Chem.—Chimica Therapeutica*, Nov. Dec. (1975) -10, No. 6, pgs. 619–622, describes sodium salts of alkenebisdithiocarbamates and aminoalkyldithiocarbamic acids for use as radiation protection agents. The compounds were tested in mice for use as radio-protectors. Particular attention is called to compound No. 11 in Table 1 on page 620, the preparation of which is described on page 621 in the paragraphs immediately below Table 2. It is believed that the structure of compound 11 is incorrectly identified. There is no disclosure or suggestion in Barnes et al., for employing any of the compounds therein for the stabilization of radiolabeled compounds and solutions.

U.S. application Ser. No. 105,272, filed Dec. 19, 1979 now U.S. Pat. No. 4,358,434 and U.S. Ser. No. 178,609, filed Aug. 15, 1980, both of which are incorporated herein by reference, disclose the stabilization of radiolabeled compounds by adding to solutions of such compounds a compound having a substantially insoluble backbone, preferably a resin, such as an ion exchange resin, to which has been bound a quaternary ammonium group; or a water soluble primary, secondary or tertiary aliphatic amine which does not interfere with the use contemplated for the particular radiolabeled compound being stabilized.

SUMMARY OF THE INVENTION

The present invention comprises a method for stabilizing a solution of a radiolabeled compound comprising adding to such solution a thiocarbonylated diethylenetriamine such, for example, as N,N-bis-(2-aminoethyl)-dithiocarbamic acid or di(2-dithiocarbamylethyl)amine, and salts thereof. The present invention also includes a solution of a radiolabeled compound maintained in contact with such a compound, and as an article of manufacture, a sealed vial containing such a solution.

These thiocarbonylated diethylenetriamines are useful for stabilizing solutions of a wide variety of labeled compounds including, for instance, amino acids, nucleotides, nucleosides, carbohydrates, drugs, lipids, steroids, and the like, labeled with tritium, carbon-14, sulfur-35, phosphorus-32, iodine-125, iodine-131, and the like.

DETAILED DESCRIPTION OF THE INVENTION

In accord with the present invention radiolabeled compounds can be stabilized by dilute solutions of a diethylenetriamine dithiocarbamic acid derivative or a soluble salt thereof. The diethylenetriamine dithiocarbamic acid derivative can be readily prepared by reacting diethylenetriamine with carbon disulfide. Particularly preferred stabilizers in accord with this invention are N,N-bis(2-aminoethyl)dithiocarbamic acid, di(2-dithiocarbamylethyl)amine, and the salts thereof, for instance, the sodium, potassium and ammonium salts.

Any amount of the stabilizer compounds of this invention is beneficial in preventing the decomposition of radiolabeled compounds. It is preferred, however, that the stabilizing compound be present at concentrations in the range of about 0.1 millimolar to about 100 millimolar depending on the specific activity of the radiolabeled compound, the concentration of the radiolabeled compound in the solution, and the particular radioisotope being employed as the label. In general, it is preferred that the concentration of stabilizing agent be $10^2$ to $5 \times 10^3$ times the concentration of labeled compound. For example a tritiated compound with a specific activity of 100 Ci/mMole at a concentration of 1 mCi/ml, would preferably contain a concentration of stabilizer in the range of about 10 to about 20 mM (a $10^3$ excess). Similarly, if the label used is phosphorus-32 which might produce a specific activity of 1000 Ci/mMole at concentration 10 mCi/ml, a ten to twenty m molar concentration of stabilizer would be preferred, i.e. a $10^3$ excess.

The method of the present invention can be used with any of the solvents typically used to store radiolabeled compounds such as water, ethanol, mixtures of water and ethanol in any ratio, dilute mineral and organic acids, and other such solvents employed in the prior art. However, some of the diethylenetriamine derivative useful in accord with this invention do not provide stability at low pH. Thus, for instance, the use of N,N-bis(2-aminoethylene)dithiocarbamic acid and di(2-thiocarbamylethyl)amine are limited by instability below pH of 6. Therefore, in general, a pH of 6 or more is preferred.

The present invention can be used to prevent the decomposition of radiolabeled compounds which have been labeled with any of the radionuclides used for such purposes, including tritium, carbon-14, phosphorus-32, phosphorus-33, sulfur-35, and the various radioisotopes of iodine, including iodine-125, and iodine-131.

The radiolabeled compound may be any of those subject to radiolytic decomposition, such as radiolabeled amino acids, catecholamines, nucleotide triphosphates, nucleosides, protein, peptides, carbohydrates, drugs, lipids, fatty acids, steroids, and the like.

Typical examples of the type of compounds included in this term "drugs" are: Abscisic acid, (±) cis, trans-[2-$^{14}$C]-; Acetaminophen; Acetyl-2-aminofluorene, N-[9-$^{14}$C]-; Acetyl Concanavalin A; Acetyl-5-methoxytryptamine, N-[2-aminoethyl-2-$^3$H]-; Acetylsalicylic acid, [carboxyl-$^{14}$C]-; α-Acid glycoprotein, [$^{125}$I]-; ACTH; Adrenocorticotropic hormone, [$^{125}$I]-(human); ADTN; Albumin (bovine serum), [$^{125}$I]-; Allynormetazocine; Alprenolol; Amethopterin; Aminoclonidine, p-[3,5-$^3$H]-; Amino-6,7-dihydroxy-1,2,3,4-tetrahydronaphthalene, 2-:-[5,8-$^3$]-; Aminopyrine, [dimethylamine-$^{14}$C]-; Amino-12,4-triazole, 3-[5-$^{14}$C]-; Amphetamine sulfate, D-[$^3$H(G)]-; Angiotensin III (4-L-isoleucine), [tyrosyl-3,5-$^3$H(N)]-; Angiotensin II (5-L-isoleucine), [tyrosyl-3,5-$^3$H(N)]-; Angiotensin II (5-L-isoleucine), [tyrosyl-$^{125}$I]-(monoiodinated); Angiotensin I (5-L-isoleucine), [tyrosyl-$^{125}$I]-(monoiodinated); Antipyrine, [N-methyl-$^{14}$C]-; Apomorphine, L-(−)-[8,9-$^3$H]-; Ascorbic acid, L-[1-$^{14}$C]-; Benzene hexachloride, γ-[$^{14}$C(U)]-; Benzidine, [$^{14}$C(U)]-; Benzo[a]pyrene, [1,3,6-$^3$H]-; Bovine serum albumin; Bradykinin, [2,3-prolyl-3,4-$^3$H(N)]-; Bradykinin (8-tyrosine)-triacetate, [8-tyrosyl-$^{125}$I]-; α-Bungarotoxin, [$^{125}$I]-; Caffeine, [1-methyl-$^{14}$C]-; Capsaicin; Carazolol, DL-[3,6-$^3$H(N)]-; Chloramphenicol, [dichloracetyl-1,2$^{14}$C]-; Chloroquine, dip[phosphate salt], [ring-3-$^{14}$C]-; Chlorpromazine hydrochloride, [benzene ring-$^3$H]-; Clonidine hydrochloride, [4-$^3$H]-; Cocaine, leyo-[benzoyl-3,4-$^3$H(N)]-; Coenzyme A, [$^3$H(G)]-; Colchicine, [ring C, methoxy-$^{14}$C]-; Colchicine, [ring C, methoxy-$^3$H]-; Concanavalin A, [$^3$H(G)]-; Concanavalin A [$^{125}$I]-; Concanavalin A, N-[acetyl-$^3$H] acetylated-; Cyclohexenyl-3,5-dimethylbarbituric acid, 5-[2-$^{14}$C]-; Cyclohexyladenosine, N$^8$-[adenine-2,8-$^3$H]-; Cyclophosphamide, [ring-4-$^{14}$C]-; Cytochalasin B, [4-$^3$H]-; Daunomycin, [$^3$H(G)]-; Daunorubicin; Desipramine; Desmethylimipramine hydrochloride, [2,4,6,8-$^3$H]-; Diazald Diazepam; 2-([2,6-Dichloro-4-amino] phenylimino)-imidazoline; Diethyl-8-phenylxanthine, 1,3-[phenyl-4-$^3$H]-; Dihydroalprenolol hydrochloride, levo-[propyl-1,2,3-$^3$H]; Dihydroalprenolol hydrochloride, levo-[ring, propyl-$^3$H(N)]-; Dihydroalprenolol, [nonanamide-6,7,9-$^3$H(N)]-; [Dihydro-a-ergocryptine, 9,10-$^3$H(N)]-; Dihydromorphine, [N-methyl-$^3$H]-; Dihydropicrotoxinin, α-[8,10-$^3$H]-; Dithydrostrychnine, [21,22-$^3$H]-; Dilantin; [2,6-Dimethoxyphenoxyethyl]aminomethyl-1,4-benzodi-oxane, 2-[phenoxy-3-$^3$H(N)] (WB4101); Dimethylbenz[a]anthracene, 1,12-[dimethyl-$^{14}$C]-; (1,3-Dimethylbutyl)-5-ethylbarblturic acid, (−)-5-[butyl-2,3,4-$^3$H]-; Dimethylhydrazine dihydrochloride, N,N-[methyl-$^{14}$C]-; Dinitrosopiperazine, N,N-[$^{14}$C(U)]-; Dioxolane, L ( )-cis, [2-methyl-$^3$H]-; Diphenylthydantoin, 5,5-[4-$^{14}$C]-; Diphenythydantoin, 5,5-[phenyl-4-$^3$H(N)]-; (−)-DMBB and (+)-DMBB; Domperidone, [benzene ring-$^3$H]-; Doxepin, [methyl-$^3$H]-; Enkephalinamide (2-D-alanine-5L-methionine), [tyrosyl-3,5-$^3$H]-; Enkephalin (2-D-alanine-5-D-leucine), [tyrosyl-3,5$^3$H(N)]-; Enkephalin (5-L-leucine), [tyrosyl-3,5-$^3$H(N)]-; Enkephalin (5-L-leucine), [$^{125}$I]-; Enkephalin (5-L-methionine), [tyrosyl-3,5-$^3$H(N)]-; Enkephalin (5-L-methionine), [$^{125}$I]-; Epidermal growth factor, [$^{125}$I]-; Ethyl β-carboline-3-carboxylate,, [ethyl-2-$^3$H]-; Ethylketazocine; Ethylketocyclazocine, [9-$^3$H]-; Ethyl-5-(1-methylbutyl)barbituric acid, 5-[ring-2-$^{14}$C]-; Ethyl-N-nitrosourea, N-[ethyl-1-$^{14}$C]-; Ethyl-5-phenyl-barbituric acid, 5-[ring-2-$^{14}$C]-; Ethyl-5-phenylbrbituric acid 5-[$^3$H(G)]-; Fibronectin, [$^{125}$I]-; Flunitrazepam, [methyl-$^3$H]-; Fluorouraci, 5-[6-$^{14}$C]-; Flurazepam, [ethylene$^3$H]-; Gelatin, [$^{125}$I]-; Gibberellin A$_1$, [3,4-$^3$H(N)]-; Glucagon, [$^{125}$I]-(monoiodinated); Gonadotrophin releasing hormone; Haloperidol, [$^3$H(G)]-; Halothane, [1-$^{14}$C]-; Heparin, sodium salt [$^3$H(G)]-; Hexabromobiphenyl, 2,4,5,2',4',5'-[$^{14}$C(U)]-; Hexachlorobenzene, [$^{14}$C(U)]-; Hexachlorobiphenyl, 2,4,5,2',4',5'-[$^{14}$C(U)]-; Hippuryl-L-histidyl-L-leucine, [glycine-1-$^{14}$C]-; Histamine dihydrochloride, [ring,methylenes-$^3$H(N)]-; Human chorionic gonadotrophin, [$^{125}$I]-; Human growth hormone, [$^{125}$I]-; Hydroxyacetanilide, p-[³H(G)]-; Hydroxybenzylisoproterenol, p-[7-³H]-; Hydroxybenzylpindolol, [¹²⁵I]-; C 125,211; Imipramine hydrochloride, [2,4,6,8-³H]-; Imipramine hydrochloride, [N-methyl-³H]-; Insulin (porcine) [¹²⁵I]-(monoiodinated); Iodoantipyrine, 4-[N-methyl-¹⁴C]-; Iodoantipyrine, 4-[¹²⁵I]-; Iodoantiptyrine, 4-[¹³¹I]-; Iodohydroxybenzylpindolol, [¹²⁵I]-; Isoguvacine hydrochloride, [³H]-; Isosorbide dinitrate, [¹⁴C]-; Lidocaine hydrochloride, [carbonyl-¹⁴C]-; Lindane; LSD; Luteinizing hormone releasing hormone, [pyroglutamyl-3,4-H]-; Luteinizing hormone releasing hormone, [¹²⁵I]-; Lysergic acid diethylamide, [N-methyl-³H]-; Melanotropin release inhibiting hormone, [L-proline-2,3,4,5-³H]-; Melatonin; Mepyramine; Methadone hydrobromide, levo-[1-³H]-; Methotrexate, [L-glutamyl-3,4-³H]-; Methscopolamine; Methyl β-carboline-3-carboxylate, [methyl-³H]-; Methylcholanthrene, 3-[6-¹⁴C]-; Methyl-D-aspartic acid, N-[methyl-³H]-; Methyl mercury chloride, [²⁰³Hg]-; Methyl-N'-nitro-N-nitrosoguanidine, N-[methyl-¹⁴C]-; Methyl-N'-nitroso-p-toluenesulfonamide, N-[methyl-¹⁴C]-; Methyl-N-nitrosourea, N-[methyl-¹⁴C]-; Methyl-N-nitrosourea, N-[methyl-³H]-; Methyl-2-phenylethyladenosine, L-N⁶-1-[adenine-2,8H, ethyl-2-³H]-; Methyl-N-vanillyl-nonanamide; 2-Methyl-4-trimethylammoniummethyl-1, 3-dioxolane iodide; Mianserin hydrochloride, [N-methyl-³H]-; MIF; Morphine, [N-methyl-³H]-; MTX; Muscimol, [methylene-³H(N)]-; Naloxone, [N-allyl-2,3-³H]-; Neurotensin, [3,11-tyrosyl-3,5-³H(N)]-; Nicotine, [pyrrolidine-2-¹⁴C]-; Nicotine, DL-[pyrrolidinyl-³H(N)]-; Nipecotic acid, [ring-³H]-; Nitrendipie, [5-methyl-³H]-; Nitrosodiethylamine, N-[ethyl-1-¹⁴C]-; Nitrosodimethylamine, N-[methyl-¹⁴C]-; Nitrosoethylmethylamine, N-[ethyl-1-¹⁴C]-; Nitroso methylurea; Nitrosonornicotine, N'[pyrrolidine-2-¹⁴C]-; Nitrosopiperidine, N-[2,6-¹⁴C]-; Nitrosopyrrolidine, N-[2,5-¹⁴C]-; N-Methyl scopolamine; Oxotremorine-M acetate, [methyl-³H]-; Pantothenic acid, sodium salt, D-[1-¹⁴C]-; Paracetamol; Parathion, [phenyl-¹⁴C]-; P[Pargyline hydrochloride, [phenyl-3, benyl-³H]-; Pentobarbital; Phencyclidine, [piperidyl-34-³H(N)]-; Phenobarbital; Phenoxybenzamine hydrochloride, [phenoxy-³H(N)]-; Phenylisopropyladenosine; Phenytoin; Phorbol-12,13dibutyrate, [20-³H(N)]-; Phorbol-12-myristate-13-acetate, [20-³H(N)]-; Piperiine-4 sulfonic acid, [ring-³H]-; Polychlorinated biphenyls (isomeric mixture), [¹⁴C(U)]-; Polychlorinated biphenyls (isomeric mixture), [¹⁴C(U)]-; Prazosin, [turoyl-5-³H]-; Prolactin (human), [¹¹⁵I]-; Prolactin (rat), [¹²⁵I]-; Prolyl-leucyl-glycinamide; Propranolol, L-[4-³H]-; Propyl β-carboline-3-carboxylate, [propyl-2,3-³H]-; Pronorapomorphine, L-(—)[N-proply-³H(N)]-; Pyrilamine, [pyrindinyl-5-³H]-; Quinuclidinyl benzilate, L-[benzillic-4,4-³H(N)]-; Rauwolscine, [methyl-³H]-; Reserpine, [benzoyl-³H(G)]-; Reverse T3; RO5-4864, [N-methyl-³H]-; Salicyclic acid, [7-¹⁴C]-; Scopolamine methyl chloride, [N-methyl-³H]-; SXF-10,047, [N-allyl-2,3-³H]-; Somatostatin, 1-tyrosine, [¹²⁵I]-monolodinated; Spiperone, [benzene ring-³H]-; Spiroperidol; Substance P (8-L-tyrosine), [¹²⁵I]-; Succinimidyl proplonate, N-[propionate-2,3-³H]-; Sulfanilic acid, [³⁶S]; Taurine, [³⁶S]-; Tetracycline, [7-³H(N)]-(free base); Tetrahydroisoxazolo(5,4-c)pyridin-3-ol,4,5,6,7-[5,7-³]-(THIP); Theophylline, [8-¹⁴C]-; Thyroid stimulating hormone (human), [¹²⁵I]-; Thyrotropin releasing hormone, [L-proline-2,3,4,5-³H(N)]-; Thyrotropin releasing hormone (3-methyl-histidine²), [L-histidyl-4-³H(N), L-prolyl-3,4-³H(N)]-; Thyrotropin releasing hormone, [¹²⁵I]-(monoiodinated); Thyroxine, L-[¹²⁵I]-; Tiotidine, [methyl-³H]-(C 125,211); Trifluoro-2-bromochioroethane; Trilodothyronine, L-3,,5,3'-[¹²⁵I]-; Trilodothyronine, L-3,3',5'-[¹²⁵I]-(Reverse T3); Tubocurarine chloride, dextro-[13'-³H(N)]-; Valium (Trademark of Hoffmann-LaRoche); Vasopressin, 8-arginine, [¹²⁵I]-; Vitamine A₁(all trans), [1-³H(N)]-; WB-4101; Xylocaine; Yohimbine, [methyl-³H]-.

The stabilizing compounds in accord with the present invention are particularly effective, with for instance, radiolabeled methionine, deoxyguanidine triphosphate and enkephalin.

Radiolabeled compounds are typically commercially distributed in closed vials containing a solution of the particular radiolabeled compound. The stabilizing compound is simply added to a solution of the radiolabeled compound which is typically shipped in a sterilized sealed vial from which the stabilized compound is removed by withdrawing with a syringe.

The invention will be further illustrated by the following examples, which are intended to be purely exemplary of the use of the invention.

EXAMPLE 1

Prior Art $^{35}S$ Methionine was stored with various prior art stabilizers and the radiochemical purity was measured over time. The methionine was from standard lots of NEN G-009H at 10 mCi/ml, in aqueous 10 mMolar 2-mercaptoethanol with specific activity greater than 1000 Ci/mM. The radiochemical purity was determined by an HPLC separation of the impurities followed by post column radioactivity quantitization. The purity values listed are an average of triplicate packagings and purity determinations. Tables 1–3 illustrate the stabilization afforded by prior art stabilizers at the indicated temperatures.

TABLE 1

Storage at −20° C.

| Sample | Starting Purity | No. of Days | Average Purity (%) | Average Change in Purity (%) |
|---|---|---|---|---|
| Control | 95 | 3 | 89 | 6 |
|  |  | 21 | 78 | 17 |
| Tris.HCl pH 7 (1 molar) | 95 | 3 | 95 | 0 |
|  |  | 21 | 93 | 2 |

TABLE 2

Storage at 4° C.

| Sample | Starting Purity | No. of Days | Average Purity (%) | Average Change in Purity (%) |
|---|---|---|---|---|
| Control | 92 | 5 | 71 | 21 |
|  |  | 11 | 57 | 35 |
|  |  | 13 | 53 | 39 |
| Polyethyleneimine (Av.M.W. 75,000; 75 mMolar in Nitrogen) | 92 | 6 | 84 | 8 |
|  |  | 11 | 76 | 16 |
|  |  | 13 | 68 | 24 |

TABLE 3

Storage at −20° C.

| Sample | Starting Purity | No. of Days | Average Purity (%) | Average Change in Purity (%) |
|---|---|---|---|---|
| Control | 92 | 7 | 80 | 6 |
|  |  | 29 | 71 | 21 |
| Tris-HCl (pH 7; | 92 | 7 | 88 | 5 |

TABLE 3-continued

Storage at −20° C.

| Sample | Starting Purity | No. of Days | Average Purity (%) | Average Change in Purity (%) |
|---|---|---|---|---|
| 50 mMolar) | | 29 | 29 | 12 |

EXAMPLE 2

Preparation of Thiocarbonylated Diethylenetriamine

To a solution of diethylenetriamine, deta(1.8 ml, 18 mM) in aqueous $NH_4OH$ (1.5%, 20 ml) was added carbon disulfide (2 ml, 33 mM) with stirring. The resulting two phase suspension was stirred four hours then diluted with water (10 ml) and filtered to afford crude thiocarbonylated diethyelenetriamine as a white solid. The crude material was washed with isopropanol (2×100 ml) and dried overnight in vacuum (40° C./20 mm) to leave the thiocarbonylated diethylenetriamine (1.83 g; M.P. 120°–121°). The material was characterized by its IR (KBr) 1460–1470 (Br, S) $cm^1$, indicative of the dithiocarbamate. The natural abundance carbon-13 NMR (d6-DMSO) contained resonances at 203.3, 182.9, 182.6 ppm downfield from tetramethylsilane indicative of dithiocarbamate. The U.V. ($H_2O$) confirmed the above assignments.

Analysis found C; 29.24: H; 6.48: N; 18.34: S; 41.42.

The material appears to be a mixture of diethylenetriamine dithiocarbamic acid derivatives formed by 1:1 and 2:1 addition of carbon disulfide to DETA affording an average molecular weight of 217. A formulation consisting of 4.5 mg/ml, thus, representing a of 20 mMolar.

The material is sparingly soluble in $H_2O$ and at acidic pH.

$^{35}S$ Methionine was stored in solution with the thiocarbonylated diethylenetriamine and the radiochemical purity was measured over time as in Example 1. Tables 4 and 5 illustrate the stabilization effectiveness of the compound of this invention.

TABLE 4

Storage at −20° C.

| Sample | Starting Purity | No. of Days | Average Purity (%) | Average Change in Purity (%) |
|---|---|---|---|---|
| Control | 89 | 6 | 86 | 3 |
|  |  | 26 | 78 | 11 |
| Tricine (pH 7; 25 mMolar) | 88 | 6 | 88 | 0 |
|  |  | 26 | 86 | 2 |
| Thiocarbonylated Diethylenetriamine (4.5 mg/mL; pH 7) | 92 | 6 | 92 | 0 |
|  |  | 26 | 90 | 2 |

TABLE 5

Storage at 4° C.

| Sample | Starting Purity | No. of Days | Average Purity (%) | Average Change in Purity (%) |
|---|---|---|---|---|
| Control | 94 | 2 | 77 | 17 |
|  |  | 4 | 64 | 30 |
|  |  | 7 | 48 | 46 |
| Thiocarbonylated Diethylene-triamine (pH 7) | 94 | 2 | 94 | 0 |
|  |  | 4 | 93 | 1 |
|  |  | 7 | 91 | 3 |
| Tricine (pH 7; 25 mMolar) | 93 | 2 | 84 | 9 |
|  |  | 4 | 77 | 16 |
|  |  | 7 | 70 | 23 |

Tables 4 and 5 illustrate the use of thiocarbonylated diethylenetriamines for effective stabilization radiolabeled compounds. Because the rapid breakdown of $^{35}S$ methionine represents an accelerated model for the radiolytic breakdown of radiolabeled compounds in solution, thiocarbonylated diethylenetriamine is useful for stabilizing other radiolabeled compounds such as those listed above.

EXAMPLE 3

Preparation of Sodium, N,N-bis-(2-aminoethyl) Dithiocarbamate

To a solution of DETA (9 ml, 88 mM) in 15% ethanolic sodium hydroxide (50 ml) at −5° C. was added carbon disulfide (10 ml, 167 mM) dropwise with stirring under a nitirogen atmosphere. The solution turned yellow and additional ethanol (50 ml) was added with stirring continued at −5° C. until a precipitate had appeared. The reaction mixture was allowed to warm to 25° C. with stirring continued 16 hours. The precipitate was collected, washed with isopropanol and dried in the vacuum oven at 40° C. for 22 min. to yield 3.6 g (20%) having a m.p. 122°–124° C.

IR (KBr) 1480 $cm^1$.

$^1H$ NMR (NaOD/$D_2O$) ppm δ4.09 (t, 1, J=7 Hz); 2.95 (t, 1, J=7 Hz).

$^{13}C$ NMR (NaOD/$D_2O$) ppm δ211.63 (c=s); 57.12; 38.84.

UV (pH 8) max 293,258 nm.

$C_5H_{13}N_3S_2Na$: theory C, 29.70; H, 6.44; N, 20.79; S, 31.68: found C, 30.13; H, 6.61; N, 20.09; S, 34.67.

EXAMPLE 4

Thiocarbonylated diethylenetriamine and N,N-bis-(2-aminoethyl)dithiocarbamate were used in various concentrations to stabilize solutions of Enkephalin (5-L-methionine) [$^3H$], a peptide, deoxyguanidine triphosphate [$^{35}P$], a nucleotidetriphosphate, and Methionine [$^{35}S$], an amino acid. The radiochemical purities were determined as in Example 1, by HPLC with quantitization by means of a post column radioactivity flow monitor. The purity values listed are an average of three samples and individual purity determinations. Tables 6–8 illustrate the stabilization effectiveness of the compounds of this invention.

TABLE 6

Storage of Deoxyguanidine triphosphate [α-$^{32}P$], 800 Ci/mol 12.8 mCi/mL, at 4° C.

| Sample | Starting Purity (%) | No. of Days | Average Purity (%) | Average Change in Purity (%) |
|---|---|---|---|---|
| Control | 90 | 1 | 9 | 81 |
|  |  | 3 | <9 | >81 |
|  |  | 9 | 0 | 90 |
| N,N—bis-(2-aminoethyl) dithiocarbamate |  |  |  |  |
| 5 mMolar | 90 | 1 | 88 | 2 |
|  |  | 3 | 75 | 15 |
|  |  | 9 | 20 | 70 |
| 10 mMolar | 90 | 1 | 88 | 2 |
|  |  | 3 | 84 | 6 |
|  |  | 9 | 53 | 37 |
| 20 mMolar | 90 | 1 | 88 | 2 |
|  |  | 3 | 83 | 7 |
|  |  | 9 | 70 | 20 |

TABLE 7

Storage of Methionine [$^{35}$S]
1004 Ci/mMol, 10 mCi/mL, 10 mCi/mL at 4° C.

| Sample | Starting Purity (%) | No. of Days | Average Purity (%) | Average Change in Purity (%) |
|---|---|---|---|---|
| Control | 88 | 3 | 72 | 16 |
|  |  | 5 | 64 | 24 |
|  |  | 10 | 47 | 41 |
|  |  | 14 | 39 | 49 |
| Thiocarbonylated | 86 | 3 | 86 | 0 |
| Diethylenetriamine |  | 5 | 86 | 0 |
| (20 mMolar) |  | 10 | 85 | 1 |
|  |  | 14 | 83 | 3 |
| Thiocarbonylated | 83 | 3 | 82 | 1 |
| Diethylene |  | 5 | 82 | 1 |
| Triamine |  | 10 | 81 | 2 |
| (10 mMolar) |  | 14 | 81 | 2 |
| Thiocarbonylated | 81 | 3 | 80 | 1 |
| Diethylene triamine |  | 5 | 80 | 1 |
| (5 mMolar) |  | 10 | 77 | 4 |
|  |  | 14 | 74 | 7 |

TABLE 8

Storage of Enkephalin (5-L-Methionine) [$^3$H], 50 Ci/mMol) at −10° C.

| Sample | Starting Purity (%) | No. of Days | Average Purity (%) | Average Change in Purity |
|---|---|---|---|---|
| Control | 99 | 27 | 92 | 7 |
|  |  | 46 | 87 | 12 |
|  |  | 67 | 84 | 15 |
|  |  | 113 | 75 | 24 |
| Thiocarbonylated | 99 | 27 | 98 | 1 |
| Deta 20 mMolar |  | 47 | 98 | 1 |
|  |  | 68 | 98 | 1 |
|  |  | 113 | 96 | 3 |

The invention has been described in detail along with the preferred embodiments thereof. However, it will be appreciated that those skilled in the art, upon consideration of this disclosure, may effect modifications and improvements within the spirit and scope of this invention.

I claim:

1. A composition comprising an admixture of a radiolabeled compound and a thiocarbonylated diethylenetriamine stabilizing agent.

2. The composition of claim 1 wherein said radiolabeled compound is selected from the group consisting of amino acids, peptides, proteins, nucleotide triphosphates, nucleosides, carbohydrates, drugs, lipids, catecholamines, fatty acids, and steroids.

3. The composition of claim 1 wherein said radiolabeled compound is labeled with tritium, carbon-14, sulfur-35, phosphorus-32, iodine-125, or iodine-131.

4. The composition of claim 1 wherein said stabilizing agent is present in an amount of about $10^2$ to $5 \times 10^3$ times the molar concentration of radiolabeled compound.

5. The composition of claim 1 wherein said stabilizing agent is present in an amount of about 0.1 m molar to about 100 m molar.

6. The composition of claim 1 wherein said stabilizing agent is N,N-bis(2-aminoethylene)dithiocarbamic acid.

7. The composition of claim 6 further having a pH of about 6 or greater.

8. The composition of claim 1 wherein said stabilizing agent is di(2-thiocarbamylethyl)amine.

9. The composition of claim 8 further having a pH of about 6 or greater.

10. The composition of claim 1 further having a pH of about 6 or greater.

11. A kit comprising a container having therein a composition as described in any one of claims 1 through 10.

12. The kit of claim 11 wherein said container is a sealed vial.

13. The kit of claim 12 wherein said vial and its contents are sterilized.

14. A method for stabilizing a radiolabeled compound said method comprising admixing with said compound a thiocarbonylated diethylenetriamine stabilizing agent.

15. The method of claim 14 wherein said radiolabeled compound is selected from the group consisting of amino acids, nucleotide triphosphate, nucleosides, protein, peptides, carbohydrates, drugs, lipids, catecholamine, fatty acids, and steroids.

16. The method of claim 14 wherein said radiolabeled compound is labeled with tritium, carbon-14, sulfur-35, phosphorus-32, iodine-125, or iodine-131.

17. The method of claim 14 wherein said stabilizing agent is present in an amount of about $10^2$ to $5 \times 10^3$ times the molar concentration of radiolabeled compound.

18. The method of claim 14 wherein said stabilizing agent is present in an amount of about 1 m mole to about 1 mole.

19. The method of claim 14 wherein said stabilizing agent is N,N-bis(2-aminoethylene)dithiocarbamic acid.

20. The method of claim 19 wherein said pH is about 6 or greater.

21. The method of claim 14 wherein said stabilizing agent is di(2-thiocarbamylethyl)amine.

22. The method of claim 21 wherein said pH is about 6 or greater.

23. The method of claim 14 wherein said pH is about 6 or greater.

* * * * *